US009421007B2

(12) United States Patent
Brady et al.

(10) Patent No.: US 9,421,007 B2
(45) Date of Patent: Aug. 23, 2016

(54) ACROMIOCLAVICULAR JOINT FIXATION USING SUTURE BUTTON CONTSTRUCT WITH DOG BONE-SHAPED BUTTON

(75) Inventors: Paul C. Brady, Knoxville, TN (US); Allen E. Holowecky, Naples, FL (US); Thomas Dooney, Jr., Naples, FL (US)

(73) Assignee: Arthrex, Inc., Naples, FL (US)

( * ) Notice: Subject to any disclaimer, the term of this patent is extended or adjusted under 35 U.S.C. 154(b) by 578 days.

(21) Appl. No.: 13/314,459

(22) Filed: Dec. 8, 2011

(65) Prior Publication Data

US 2012/0150203 A1    Jun. 14, 2012

Related U.S. Application Data

(60) Provisional application No. 61/421,383, filed on Dec. 9, 2010, provisional application No. 61/421,389, filed on Dec. 9, 2010.

(51) Int. Cl.
*A61B 17/04* (2006.01)
*A61F 2/08* (2006.01)
*A61B 17/06* (2006.01)

(52) U.S. Cl.
CPC ........... *A61B 17/0401* (2013.01); *A61F 2/0811* (2013.01); *A61B 17/06* (2013.01); *A61B 2017/0404* (2013.01); *A61B 2017/0409* (2013.01); *A61B 2017/0475* (2013.01); *A61B 2017/0477* (2013.01); *A61B 2017/0496* (2013.01); *A61F 2002/0852* (2013.01); *A61F 2002/0882* (2013.01)

(58) Field of Classification Search
CPC ................ A61B 17/0401; A61B 2017/0404; A61B 2017/0409; A61B 2017/0475; A61B 2017/0477; A61B 2017/0496; A61F 2/0811; A61F 2002/0852; A61F 2002/0882
USPC ......................... 606/232, 300, 103, 139, 144; 623/19.11; 128/898
See application file for complete search history.

(56) References Cited

U.S. PATENT DOCUMENTS

| 2,199,025 A | 4/1940 | Conn |
| 3,409,014 A | 11/1968 | Shannon |

(Continued)

FOREIGN PATENT DOCUMENTS

| AU | 2008229746 A1 | 10/2008 |
| EP | 1 645 247 A1 | 4/2006 |

(Continued)

*Primary Examiner* — Julian W Woo
*Assistant Examiner* — Lucas Paez
(74) *Attorney, Agent, or Firm* — Blank Rome LLP

(57) ABSTRACT

Methods and systems for AC joint repair using a fixation device having a specific "dog bone" configuration in a minimally invasive approach. One AC fixation system is formed of dog bone shaped buttons and at least one suture tape used to secure the buttons during an AC joint repair. The buttons are provided with openings that allow the passage of suture/tape limbs. Another AC joint fixation system is formed of a metal button inserted over a fused/joined construct having multiple flexible strands. The fused/joined construct is formed of multiple independent and separate suture strands and/or suture tapes that are joined (fused together) at about the midpoint of the tapes and/or sutures, resulting in multiple independent limbs of suture/tape. A suture tape loop construct having an integrally formed eyelet at one end of the loop may also be used in the fixation systems.

10 Claims, 18 Drawing Sheets

(56) References Cited

U.S. PATENT DOCUMENTS

| | | | |
|---|---|---|---|
| 5,417,699 A | 5/1995 | Klein et al. | |
| 6,514,274 B1* | 2/2003 | Boucher et al. | 606/232 |
| 6,533,802 B2* | 3/2003 | Bojarski et al. | 606/232 |
| 7,235,091 B2 | 6/2007 | Thornes | |
| 7,892,256 B2 | 2/2011 | Grafton et al. | |
| 8,162,997 B2* | 4/2012 | Struhl | 606/300 |
| 8,512,376 B2* | 8/2013 | Thornes | 606/232 |
| 2005/0251209 A1 | 11/2005 | Saadat et al. | |
| 2007/0016208 A1 | 1/2007 | Thornes | |
| 2007/0179531 A1 | 8/2007 | Thornes | |
| 2007/0270804 A1* | 11/2007 | Chudik | 606/60 |
| 2008/0195148 A1 | 8/2008 | Cook et al. | |
| 2009/0182335 A1* | 7/2009 | Struhl | 606/60 |
| 2010/0125297 A1* | 5/2010 | Guederian et al. | 606/232 |
| 2010/0211075 A1 | 8/2010 | Stone | |
| 2010/0262185 A1 | 10/2010 | Gelfand et al. | |
| 2011/0137341 A1 | 6/2011 | Thornes et al. | |
| 2012/0123541 A1* | 5/2012 | Albertorio et al. | 623/13.14 |

FOREIGN PATENT DOCUMENTS

| | | |
|---|---|---|
| EP | 2 455 001 A2 | 5/2012 |
| WO | WO 02/091959 A1 | 11/2002 |
| WO | WO 2004/037094 A2 | 5/2004 |
| WO | WO 2008/091690 A1 | 7/2008 |
| WO | WO 2010/046895 A1 | 4/2010 |

* cited by examiner

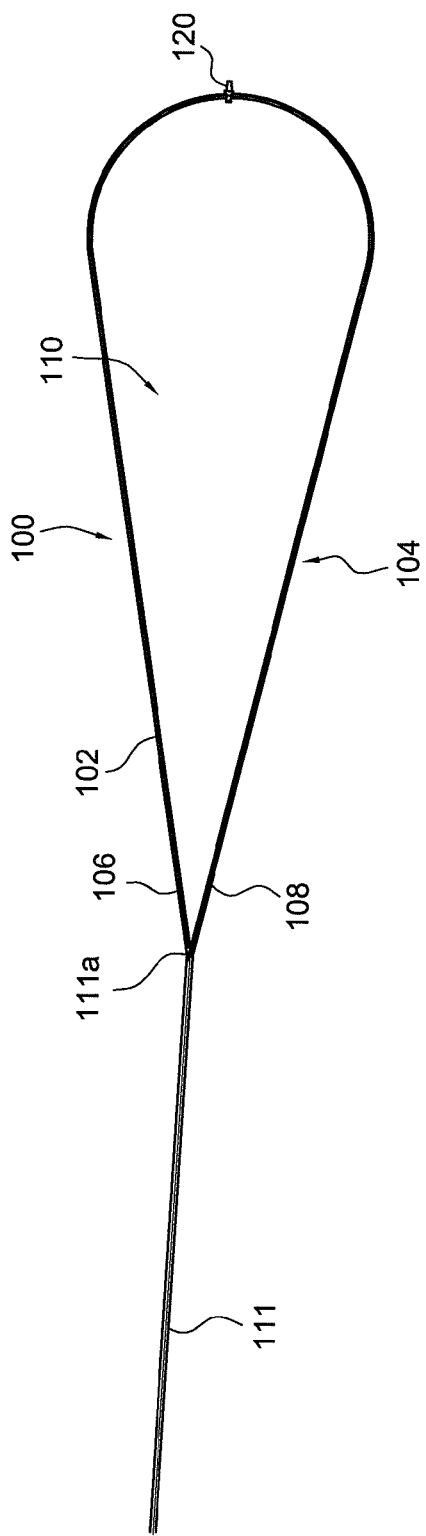
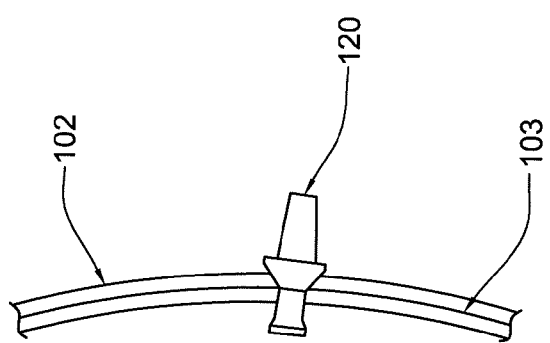

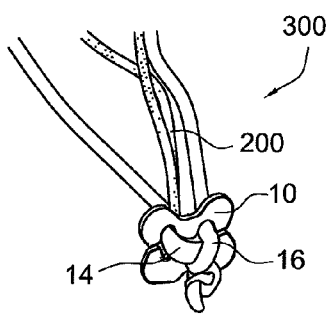
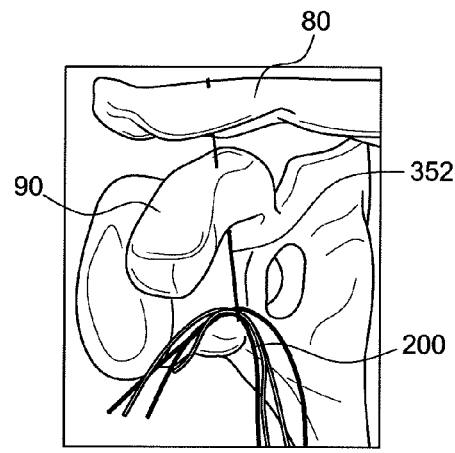
FIG. 14     FIG. 15
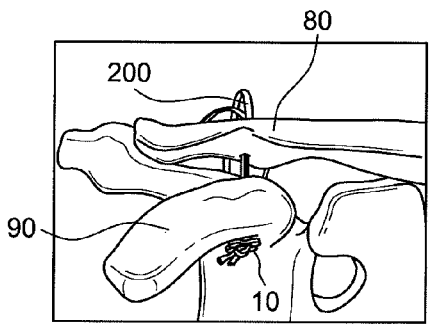
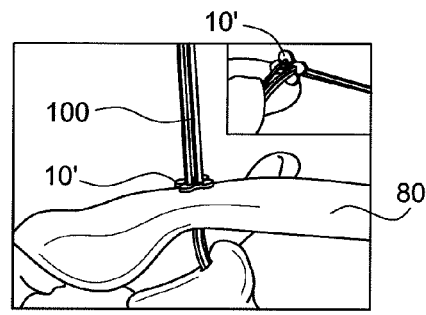
FIG. 16     FIG. 17
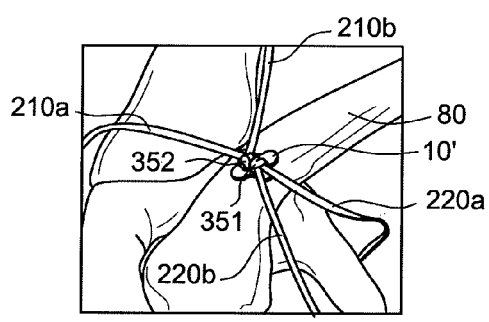
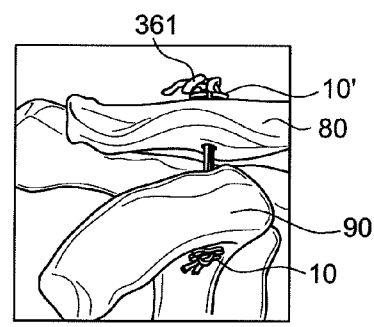
FIG. 18     FIG. 19

ACROMIOCLAVICULAR JOINT FIXATION USING SUTURE BUTTON CONTSTRUCT WITH DOG BONE-SHAPED BUTTON

CROSS-REFERENCE TO RELATED APPLICATIONS

This application claims the benefit of U.S. Provisional Application No. 61/421,383, filed Dec. 9, 2010, and U.S. Provisional Application No. 61/421,389, filed Dec. 9, 2010, the entire disclosures of which are incorporated by reference herein.

FIELD OF THE INVENTION

The present invention relates to the field of surgery and, more particularly, to an acromioclavicular (AC) joint fixation technique and associated fixation devices.

BACKGROUND OF THE INVENTION

Disruption of the coracoclavicular ligaments is a common occurrence. In many cases, the injury can be treated conservatively and the only residual problem is that of a mild cosmetic deformity. Several groups of patients, however, do not tolerate the injury well. If the joint is reduced acutely and held reduced during the healing phase, the native ligaments may heal restoring the stability of the joint.

An AC joint repair system using a suture button graft construct formed of oblong button and one round button connected by high strength suture strands and including a graft, i.e., the GraftRope®, is sold by Arthrex, Inc. of Naples, Fla. and disclosed in U.S. Patent Application Publication No. 2010/0125297, incorporated by reference herein. This system requires large 4-6 mm tunnels drilled through the bones (i.e., the clavicle and the coracoid) that pose potential fractures for the clavicle and coracoid. In addition, the four strands of high strength suture or suture tape on the outside of the graft may interfere with the graft incorporation. If the high strength strands attached to the buttons break, device and/or graft fixation is compromised. Further, if the traction suture (which is attached to the oblong button, for pulling the graft through the tunnels) breaks during the pull (due to difficulty of passing the graft though tunnels in the clavicle and coracoid), the graft can get stuck under the clavicle. Friction can also be created on the oblong button (seated against the coracoid) by the two loops of high strength suture traveling in different directions and around the oblong/coracoid button. Securing this oblong/coracoid button can also be difficult.

Another AC joint repair system sold by Arthrex, Inc. is the AC TightRope®, which is disclosed in U.S. Patent Application Publication No. 2007/0179531, the disclosure of which is incorporated by reference herein. The AC TightRope® has a similar suture-button construct as the GraftRope®, but is smaller and does not include a graft. A hole is drilled through the clavicle and the coracoid. The oblong button of the construct is passed through the holes in the clavicle and coracoid until it exits the coracoid base, and the oblong button flips onto the underside of the coracoid. The suture tails of the construct are then tightened to advance the round button down to the surface of the clavicle, and the sutures are tied to stabilize the acromioclavicular (AC) joint. Although the above-described technique and the associated suture button construct works well to stabilize the AC joint, it would be desirable to provide a construct and technique with increased fixation strength.

An improved AC fixation device and technique is needed that provides the superior strength of the GraftRope®, but without the aforementioned disadvantages. The improved technique for AC joint repair would ideally require small holes, a button that contours to the convexity of the bones (i.e., the clavicle and the coracoid), and would include secondary fixation in the clavicle and the subcoracoid to reduce the risk of device loss in case of suture breakage.

SUMMARY OF THE INVENTION

The present invention provides techniques and systems for AC joint repair with the above-noted advantages. One AC joint fixation system of the present invention comprises at least one button in the shape of a "dog bone" as part of a suture-button construct. The "dog bone" button has a concavity that approximates the convexity of the undersurface of the coracoid or the upper surface of the clavicle. The suture construct may include high strength suture strands or tape to connect the buttons and an allograft in a suture-button-allograft construct. The suture construct may be a suture tape loop having a flexible loop of suture tape material at one end and a spliced tail region at another end. In one example embodiment, an eyelet may be integral with the flexible loop.

An exemplary method of AC joint repair employing at least one "dog bone" button and at least one suture tape loop includes inter alia the steps of: (i) drilling tunnels through the coracoid and clavicle; (ii) attaching a first "dog bone" button to the at least one suture tape loop; (iii) passing a tail end of the at least one suture tape loop through the clavicle and coracoid tunnels; (iv) pulling the suture tape loop to secure the first "dog bone" button underneath the coracoid; (v) opening the at least one suture tape loop to create suture limbs; (vi) securing a second "dog bone" button over the clavicle tunnel by securing the suture tape limbs over the second "dog bone" button; and (vii) pulling on the suture tape limbs to secure fixation of the clavicle.

Another AC joint fixation system of the present invention comprises a metal button inserted over a fused/joined construct formed of fused/joined flexible strands. The fused/joined construct may be formed of multiple independent and separate suture strands and/or suture tapes that are joined (fused together) at about the midpoint of the tapes and/or sutures, resulting in multiple independent limbs of suture/tape. In an exemplary and illustrative-only embodiment, the fused/joined construct is a fused/joined suture construct formed of two independent and separate suture strands or suture tapes that are joined (fused together) at about the midpoint of both tapes or sutures, resulting in four independent limbs of suture/tape. The button, which may be a "dog bone" shaped button, is provided with openings that allow the passage of the suture/tape limbs.

The present invention also provides a method of AC joint repair by inter alia: (i) attaching a first button to a fused suture construct having four limbs so that all four limbs are of about equal length; (ii) passing the first button and the attached fused suture construct through tunnels drilled in the coracoid and the clavicle, shuttling the limbs through the tunnels, and pulling on the limbs until the first button rests against the base of the coracoid; (iii) attaching a second button over the limbs of the fused suture construct and reducing the second button to the clavicle; and (iv) securing the first and second buttons to the coracoid and the clavicle, respectively, by knotting the limbs over the second button.

Another exemplary method of AC joint repair employing at least one "dog bone" button and at least one high strength suture tape together with one graft (allograft) includes inter alia the steps of: (i) drilling tunnels through the coracoid and clavicle; (ii) passing a suture tape and a graft through the clavicle and coracoid tunnels; (iii) opening up a hole in the suture tape and the graft and placing a first "dog bone" button through the hole in the suture tape and graft, to secure the first "dog bone" button under the coracoid; (iv) securing a second "dog bone" button over the clavicle and an interference screw; and (v) providing secondary fixation of the first "dog bone" button under the coracoid by tying the suture tape limbs over the "dog bone" button to get compression, and passing the two limbs of the graft over one another, and over the "dog bone" button, and tying the two graft limbs together using a suture, for example.

These and other features and advantages of the present invention will become apparent from the following description of the invention that is provided in connection with the accompanying drawings and illustrated embodiments of the invention.

BRIEF DESCRIPTION OF THE DRAWINGS

FIGS. 10-11 illustrate a suture loop construct in accordance with an example embodiment of the present invention.

FIGS. 14-19 illustrate steps of a method of AC joint fixation using the fixation system of FIG. 13.

DETAILED DESCRIPTION OF THE INVENTION

The present invention provides methods and systems for AC joint repair and/or fixation using a fixation device (having a specific "dog bone" configuration) in a minimally invasive approach.

Figure 1:
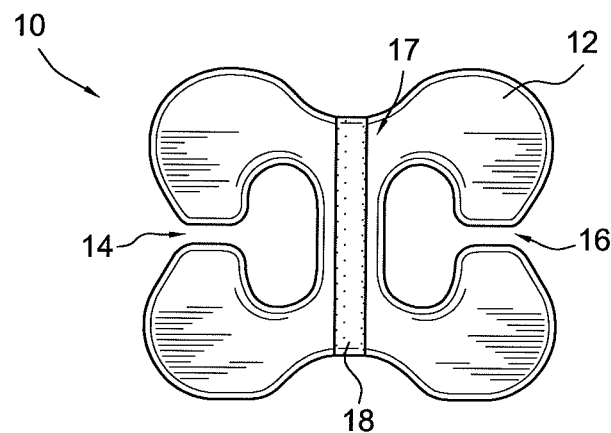
FIG. 1 illustrates a schematic view of an exemplary fixation device (button) of the present invention, having a "dog bone" shape or configuration.

Referring now to the drawings, where like elements are designated by like reference numerals, FIG. 1 illustrates a schematic view of a fixation device or button 10 having the shape of a typical "dog bone" or "dog bone" shaped treat (hereinafter simply referred to as a "dog bone shape"). The button 10 has a dog bone shaped body 12 that is preferably constructed of a metal such as titanium, but may also be formed of plastic material such as e.g., PEEK or PLLA. The body 12 may be about 12 mm×8 mm and contains two slotted openings 14, 16 that allow sutures, suture tapes, grafts, etc. to pass through the body 12. An orientation line 18 is formed on a middle portion 17 of the body 12, between the two openings 14, 16. As mentioned above, the body 12 of the dog bone shaped button 10 has a concavity that approximates the convexity of the coracoid or clavicle, which keeps the button 10 from sticking out after it has been implanted in the patient.

FIGS. 2-9 illustrate steps of an exemplary AC joint repair method using the dog bone shaped button 10 of FIG. 1.

Figure 2:
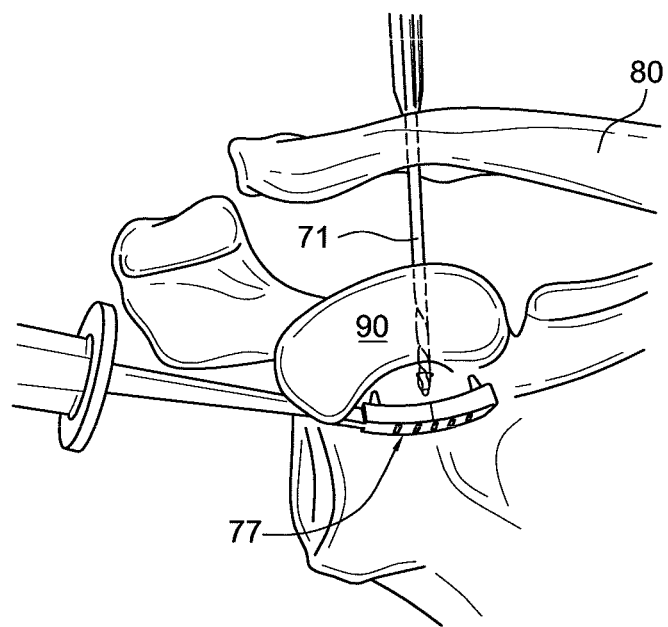
FIGS. 2-9 illustrate a method, and devices used therein, of AC joint fixation in accordance with a first example embodiment of the present invention.

Referring to FIG. 2, using an appropriate AC guide 77, tunnels are drilled into the clavicle 80 and coracoid 90 using a cannulated reamer 71. In the illustrated embodiment, the reamer 71 is a 3 mm reamer.

Figure 3:
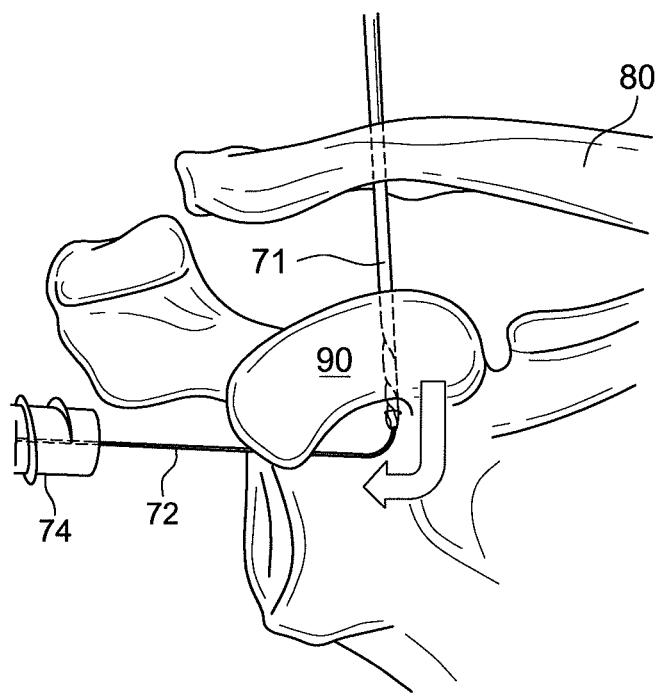
Figure 4:
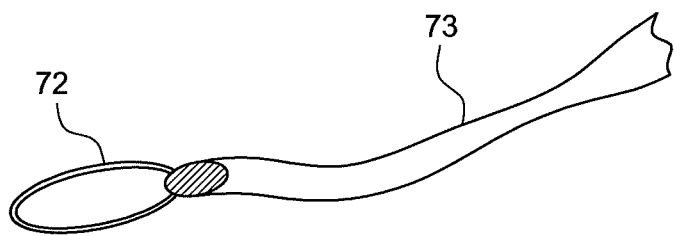

Referring to FIGS. 3 and 4, the trocar is removed from the reamer 71 and then a small diameter (SD) lasso wire 72 is passed through the reamer 71, loop first, and retrieved through the anterior cannula 74. A SD lasso instrument 73 having a suitable lasso wire 72 is shown in FIG. 4 and can be a SutureLasso™ SD sold by Arthrex, Inc. of Naples, Fla. At this point, the cannulated reamer 71 is removed.

Figure 5:
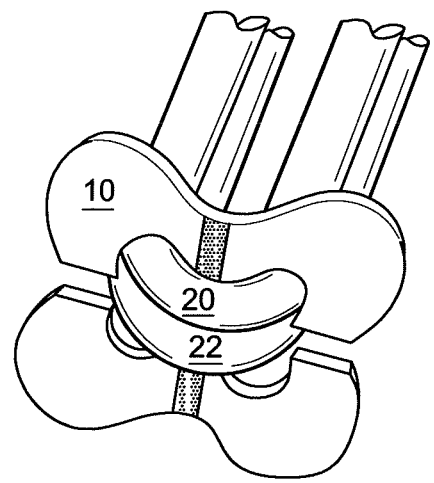

As shown in FIG. 5, two suture tape loops 20, 22 are passed through the openings of the dog bone shaped button 10. In a preferred embodiment, the suture tape loops 20, 22 are FiberTape® loops manufactured by Arthrex, Inc. of Naples, Fla., an example of which is disclosed in U.S. Patent Application Publication No. 2010/0160962, filed on Dec. 23, 2009, the disclosure of which is incorporated by reference in its entirety herein. Generally, as shown in U.S. Patent Application Publication No. 2010/0160962, each suture tape loop 20, 22 comprises a piece of suture tape that has its tail ends spliced or joined together to form a flexible loop of suture tape connected to a spliced tail. When the spliced tail region is cut, the open loop forms two limbs, which may then by tied together around a fixation device such as e.g., the button 10 (described in more detail below with reference to FIGS. 8 and 9).

Figure 6:
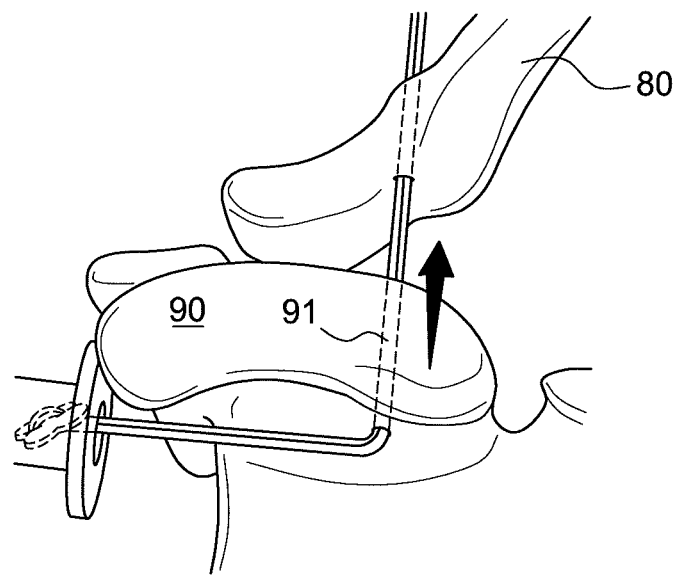

As shown in FIG. 6, the button 10 is turned sideways to help pass through the cannula. The suture tape loops 20, 22 are pulled through the coracoid tunnel 91 and clavicle tunnel 81 as shown by the arrows. Any type of grasping instrument may be used to aid in button deployment.

Figure 7:
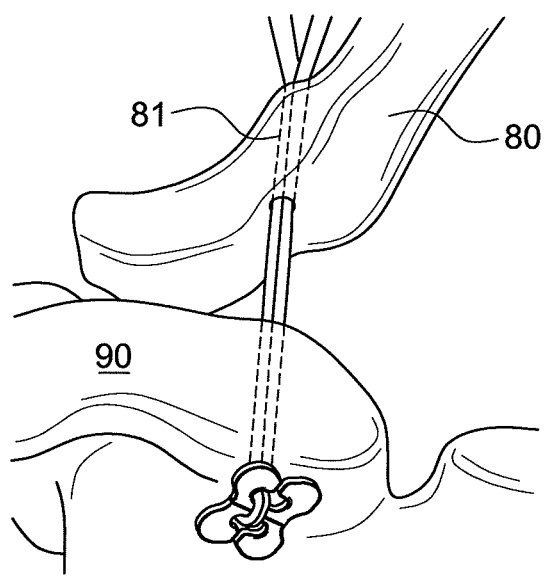

Referring now to FIG. 7, the button 10 is seated at the base of the coracoid 90. The concavity of the button's body 12 should face the coracoid 90 and the orientation line 18 should be in line with the arch of the coracoid 90.

Figure 8:
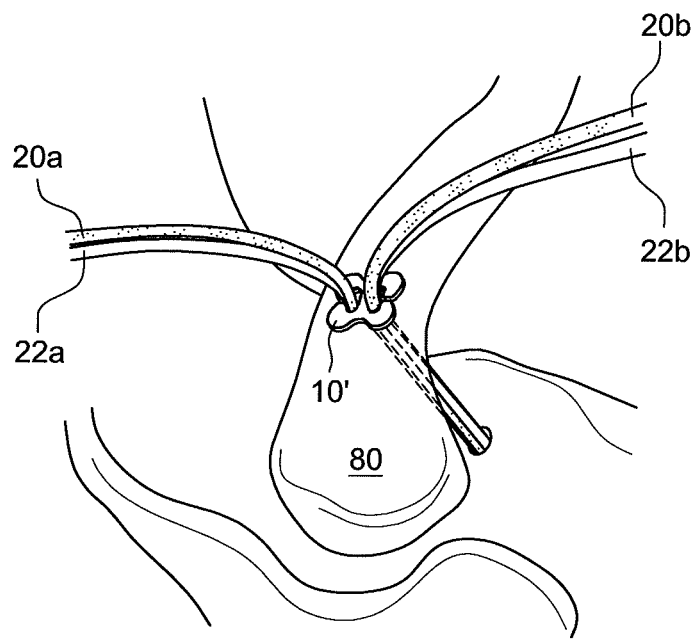

Referring to FIG. 8, the suture tape loop splices are cut to create individual suture tape limbs 20a, 20b, 22a, 22b. The suture tape limbs 20a, 20, 22a, 22b are then passed through the openings of a second dog bone shaped button 10'. The concavity of the second button's body should face the clavicle 80 and the orientation line 18 should be in line with the axis of the clavicle 80.

Figure 9:
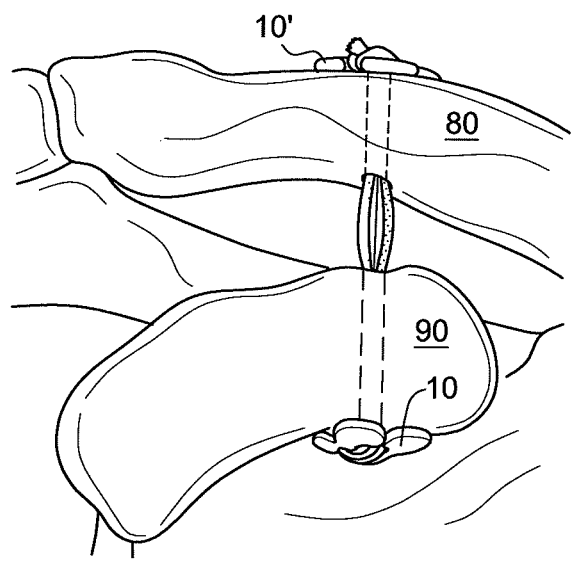

Referring to FIG. 9, the suture tape limbs 20a, 20b, 22a, 22b are reduced and tied over the second button 10' using e.g., four alternating half-hitches. It may be desirable at this point to pass the suture limbs 20a, 20b, 22a, 22b through posterior periosteum to help the knot stacks lie flat. The procedure is completed by cutting the suture limbs 20a, 20b, 22a, 22b to complete the repair.

As noted above, suture tape loops 20, 22 are used in the exemplary AC joint repair method illustrated in FIGS. 2-9. The suture tape loops 20, 22 may be FiberTape® loops manufactured by Arthrex, Inc. of Naples, Fla., an example of which is disclosed in U.S. Patent Application Publication No. 2010/0160962. Alternatively, one or more of the loops 20, 22 may be a suturing construct 100 illustrated in FIGS. 10 and 11, if desired.

As shown in FIGS. 10 and 11, the suturing construct 100 is formed of a flexible strand 102 with a middle region 104 (i.e., suture section 104), which is adjacent two tail regions 106, 108 and a splice (or single tail) 111. The diameter of tail region 106 may be similar to or different than the diameter of tail region 108. In any event, each of the diameters of the tail regions 106, 108 is smaller than the diameter of the middle region 104.

In an exemplary embodiment, the middle region 104 of the suturing construct 100 has a gradual taper in diameter (for example, from a #2 to #0 from section 104 to sections 106, 108 and single tail 111) made on a braiding machine. The single tail 111 of the construct 100 may be formed by splicing together the tail regions 106, 108 through splice 111a. The splice 111a may be done in a manner that provides a smooth transition. In another embodiment, the splice 111a and the single tail 111 may be formed by joining together at least a portion of each of tail regions 106, 108 to form flexible loop 110 and single tail 111. The joining of at least a portion of each of tail regions 106, 108 may be accomplished by braiding the tail regions, or by gluing them, or by other known method in the art. As a result of the smaller diameter of the tail regions 106, 108, and of the single tail 111, the suturing construct 100 is more easily threaded through a suture passing instrument, and passed through tissue.

The middle section 104 may have cross-sections of various forms and geometries, including round, oval, rectangular, or flat, among others, or combination of such forms and geometries. In an exemplary embodiment only, section 104 may be provided as a combination of a suture tape 102 with a round suture 103 providing additional strength to the section 104. It should be appreciated that the section may comprise only suture tape (e.g., FiberTape® as disclosed in U.S. Pat. No. 7,892,256) or a rounded suture (e.g., FiberWire® suture, sold by Arthrex, Inc. of Naples, Fla., and disclosed in U.S. Pat. No. 6,716,234), if desired. The diameter of middle section 104 may be constant or may vary. Preferably, the diameter of section 104 is constant and is greater than the diameter of sections 106, 108 and of the spliced single tail 111.

The suturing construct 100 also includes an eyelet 120 formed at the end of the loop 110 furthest from the splice 111. The eyelet 120 may be formed of plastic material such as e.g., PEEK or PLLA. The eyelet 120 may be used to engage e.g., additional suturing material, a graft or a fixation device (e.g., button 10).

In another exemplary embodiment, an AC joint fixation system of the present invention comprises two fixation devices (for example, button 10) joined by a fused/joined construct. The fused/joined construct may be formed of at least two independent and separate sutures and/or suture tapes and/or combination of sutures and suture tapes that are joined (fused together) at about the center of the sutures and/or tapes, resulting in multiple independent limbs of suture/tape.

According to an exemplary and illustrative-only embodiment, the fused/joined construct of the present invention may be formed by joining/fusing together two separate, independent suture strands. The sutures may be FiberWire® suture, sold by Arthrex, Inc. of Naples, Fla., and disclosed in U.S. Pat. No. 6,716,234, the disclosure of which is incorporated by reference in its entirety herein. The sutures may have the same or different diameters and may comprise the same or different materials. The sutures may preferably have the same length, and may have the same or different cross-sections, for example, round, oval, square, etc.

According to another exemplary embodiment, the fused/joined construct may be formed by fusing (joining together) two separate and independent suture tapes, at least one of them being a FiberTape® as disclosed in U.S. Pat. No. 7,892,256, issued Feb. 22, 2011, the disclosure of which is incorporated by reference in its entirety herein. The suture tapes are joined (fused together) at about the midpoint of both suture tapes, resulting in four independent limbs of suture tape. The suture tapes may have the same or different widths, and may comprise the same or different materials.

The fused/joined construct may consist essentially of suture or suture material, or of combination of suture and other materials such as long chain synthetic polymers like polyester and nylon, or materials such as PET, silk nylon or absorbable polymers, or coating materials (such as wax, silk, or silicone products), among many others. These materials augment the strength and pliability of the construct, and improve the characteristics and properties of the suture material. For example, one flexible strand of the fused/joined construct may consist essentially of suture or suture tape whereas the other strand of the fused/joined construct may consist essentially of nylon or polymeric material.

Joining/fusing of the suture tapes and/or suture strands may be accomplished by stitching, splicing or by known fusion techniques wherein heat or other energy is applied to the overlapped tapes or suture strands to melt at least a portion of overlapped region of the tapes/suture strands to form a fused region. If braided or multi-filament sutures/tapes are used, the fused/joined construct may be formed by overlapping the two sutures/tapes (by passing one tape/strand through the other tape/strand or over the other tape/strand, for example, to form an overlapped or connecting region), and securing the overlapped region (by suturing, for example) to lock the construct. If splicing is employed, one flexible strand (suture strand) is spliced through the other flexible strand (suture strand), for example, through the midpoint of the other flexible strand, to form a spliced region (an overlapped or connecting region). The spliced region may be additionally reinforced by suturing, for example, to lock the construct.

Figure 12B:
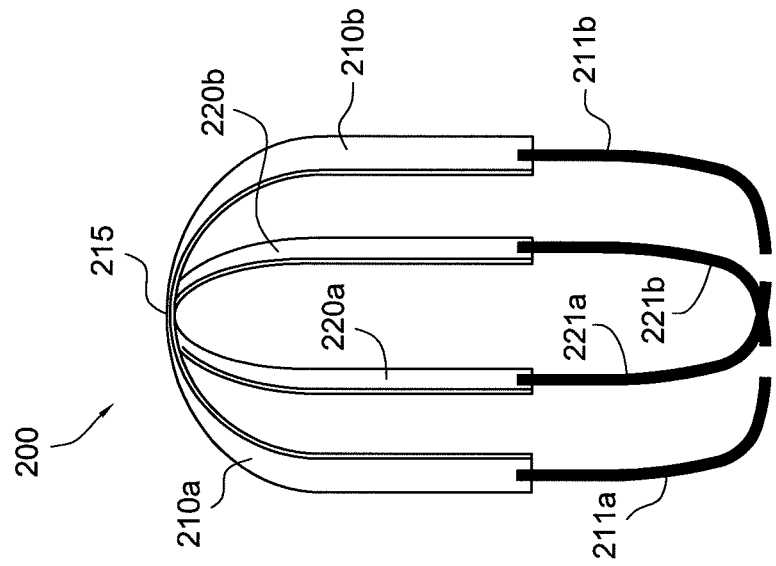
FIGS. 12(a) and 12(b) illustrate schematic views of an exemplary fused/joined suture construct of the present invention formed by fusing together two independent and separate suture tapes.
Figure 12A:
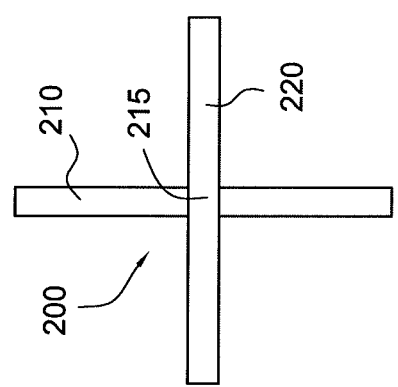

Referring now to the drawings, where like elements are designated by like reference numerals, FIGS. 12(a) and 12(b) illustrate schematic views of an exemplary fused suture construct 200 of the present invention, including fused suture strands and/or suture tapes.

The exemplary only embodiment shown in FIGS. 12(a) and 12(b) includes two suture tapes 210, 220, for example, two FiberTapes®, that are connected (joined or fused together) at the midpoint 215 of both suture tapes (as shown in FIG. 12(b)). The midpoint 215 represents an overlapped/connecting region formed by fusing together at least a portion of tape 210 and at least a portion of tape 220. Suture limbs or suture tape limbs 210a, 210b, 220a, 220b extend from the joined/overlapped/connecting region 215 resembling limbs of a squid, as shown in FIG. 12(b), i.e., with elongated arms 210a, 210b, 220a, 220b extending from the region 215 and moving freely relative to this central/common region 215 (fused/joined/connecting region 215). Transition regions 211a, 211b, 221a, 221b are also shown in FIG. 12(b) as extending from a respective end of arms or limbs 210a, 210b, 220a, 220b (i.e., from the ends opposite to those adjoining the fused/joined/connecting region 215). In the exemplary embodiment of two FiberTapes® 210, 220, the transition regions 211a, 211b, 221a, 221b may be lengths of suture strands and are provided at the end of the flat braided tape section, which is shorter than the length of suture. The transition sections are preferably tapered to allow the suture tape to pass easily through openings during surgical procedures and to also pass the holes of the fixation devices (i.e., buttons).

In the exemplary embodiment shown in FIG. 12(a), the fused/joined/connecting region 215 has a square configuration (when viewed from a top view) resulting from the FiberTapes® 210, 220 having a similar width. The fused/joined/connecting region 215 may have, however, various configurations such as rectangular, or parallelepiped, for example, depending on the manner of fusing/attaching/joining the flexible members together. The fused/joined/connecting region 215 has a thickness which is about equal to the resulting thickness of the two suture tapes (i.e., the sum of the thickness of the first suture tape 210 and of the thickness of the second suture tape 220). If multiple flexible strands are employed (such as multiple suture tapes) the thickness of the fused/joined/connecting region 215 is about equal to the sum of the thickness of each of the multiple flexible strands that are joined.

Figure 13:
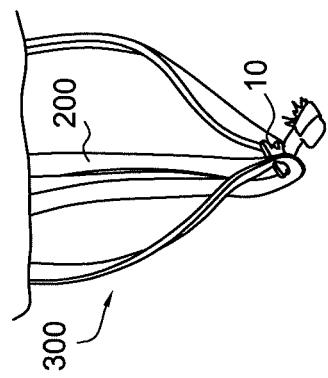
FIG. 13 illustrates an exemplary fixation system of the present invention, with the fused/joined suture construct of FIGS. 12(a)-12(b) attached to the button illustrated in FIG. 1.

FIG. 13 shows an exemplary AC fixation system 300 formed of a fused suture construct (such as the fused construct 200 of FIGS. 12(a) and 12(b)) attached to a fixation device 10, for example, a dog bone shaped button 10 illustrated in FIG. 1. The system 300 may be used in another method of AC joint fixation discussed below with reference to FIGS. 14-19.

Referring to FIG. 14, a first button 10 is inserted over the fused suture construct 200, ensuring that all four suture tails or limbs 210a, 210b, 220a, 220b of the fused suture construct 200 are of about equal length. Suture tails or limbs may be of various colors, or may be provided with optional colored strands and color traces, to distinguish the limbs among themselves and to aid medical personnel in distinguishing between limbs (suture lengths) with the trace and limbs (suture lengths) without the trace and in helping with tying of knots (as detailed below).

As shown in FIG. 15, clavicle and coracoid tunnels are drilled within the clavicle 80 and coracoid 90. A Nitinol wire 352 is passed to shuttle the limbs of the fused suture construct 200 retrograde through both tunnels.

As shown in FIG. 16, the limbs of the fused suture construct 200 are pulled until the button 10 seats against the base of the coracoid 90.

Referring to FIG. 17, a second button 10' is attached over the limbs of the fused suture construct 200 and the button 10' is reduced to the clavicle 80.

As shown in FIG. 18, the necessary reduction is obtained and each of the corresponding limbs 210a, 210b, 220a, 220b are tied together over the button 10' to form two knots 351 and 352.

As shown in FIG. 19, both knots 351, 352 are tied together to form one know stack 361 and to complete the repair.

In an exemplary embodiment, at least one of the buttons 10, 10' (preferably both buttons 10, 10') is the slotted dog bone shaped button 10 illustrated in FIG. 1, which can be removably attached to the four limbs of the fused suture construct 200.

The suture tapes 210, 220 may be used in conjunction with a flexible strand such as FiberWire® suture, which contains a high strength suture material with surgically-useful qualities and which is sold by Arthrex, Inc. of Naples, Fla., and disclosed in U.S. Pat. No. 6,716,234. The suture tapes 210, 220 may be a FiberTape® as disclosed in U.S. Pat. No. 7,892,256, issued Feb. 22, 2011. As detailed in U.S. Pat. No. 7,892,256, the suture tape is made of high strength surgical suture material and comprises a length of suture supporting a tape section of material having a flattened profile and a width greater than a thickness of the length of suture. Preferably, the length of suture extends continuously through and beyond either end of the tape section. The tape section is provided as a flat braid added to the length of suture or the flat braid may be formed around the length of suture. The flat braid may be supported along a central portion of the length of suture. The flat braid is shown in FIG. 13, for example.

Transition sections may be developed at either end of the flat braided tape section, which is shorter than the length of suture. The transition sections are preferably tapered to allow the suture tape to pass easily through openings during surgical procedures and to also pass the holes of the fixation devices (i.e., buttons).

The flexible strands forming the fused/joined construct of the present invention (such as suture strands, suture tapes, combinations of suture strands and tapes, etc.) may be coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the braid, knot security, pliability, handleability or abrasion resistance, for example. For example, a coating may be provided to the yarns forming the braided suture tapes before braiding. Similarly, the suture tails (extending from the transition regions of the suture tapes) may be coated using the same or different coating material.

In an exemplary embodiment, the suture tapes are flat braided tapes extending along a length of round suture. The flat tapes have ends terminating in tail regions of sutures (having a small diameter and which may be coated, impregnated, or otherwise stiffened with a material such as plastic, for example).

FIGS. 20-29 illustrate the steps of another method of AC joint repair. The method uses at least one dog bone shaped button 10 and at least one suture tape 420 (similar to the one described above with reference to FIGS. 12-21) but also with a graft construct 460 (for example, an allograft). According to this technique, both the suture tape 420 and the graft 460 are passed together through the clavicle and coracoid tunnels and secured to two dog bone shaped buttons 10.

Figure 20:
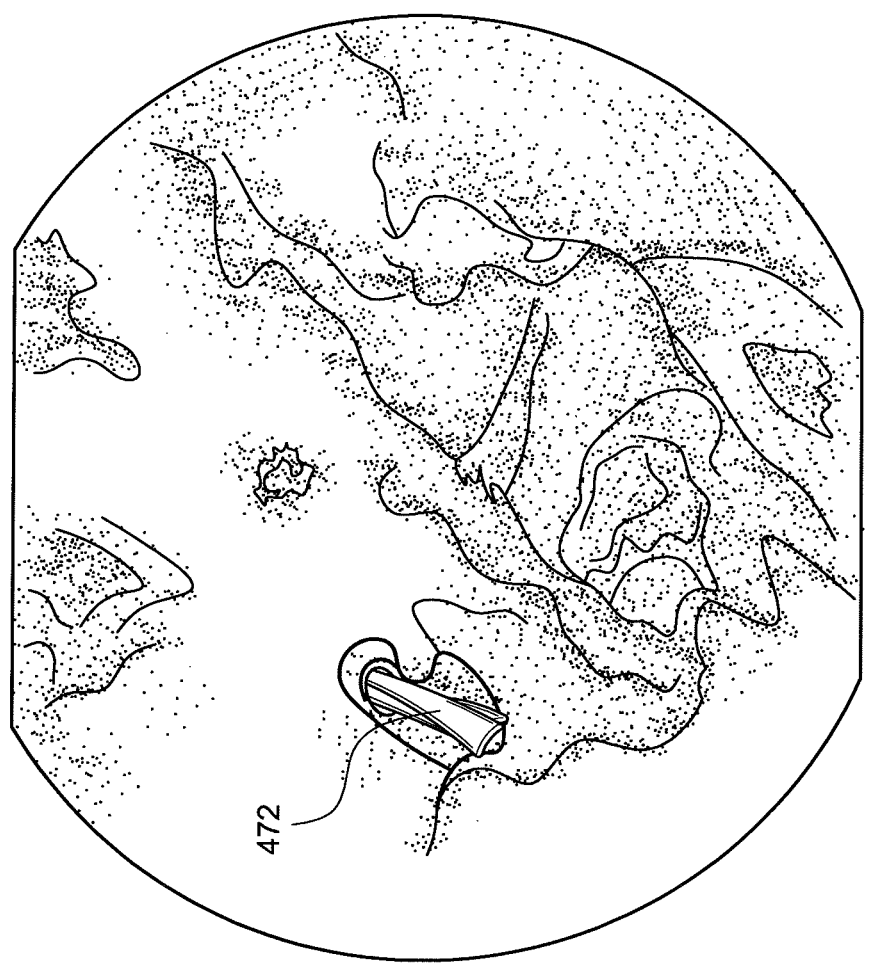
FIGS. 20-29 illustrate steps of a method of AC joint repair using at least one "dog bone" shaped button, and at least one suture tape together with a graft.

Referring now to FIG. 20, the formation of the tunnel close to the base of the coracoid (showing the tunnel on the left and with a 4 mm drill on the right) is shown.

Figure 21:
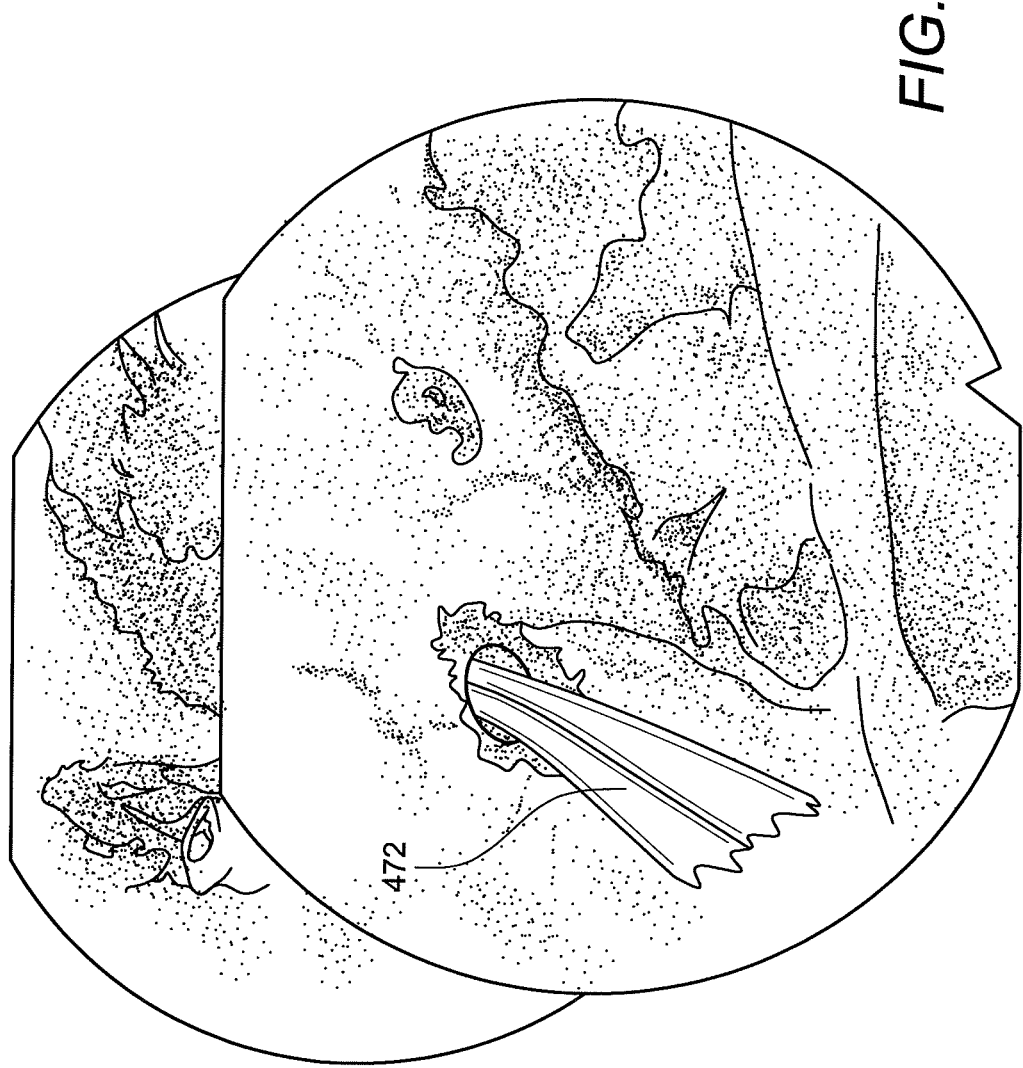

As shown in FIG. 21, a nitinol wire with attached suture 472 is passed through the coracoid.

Figure 22:
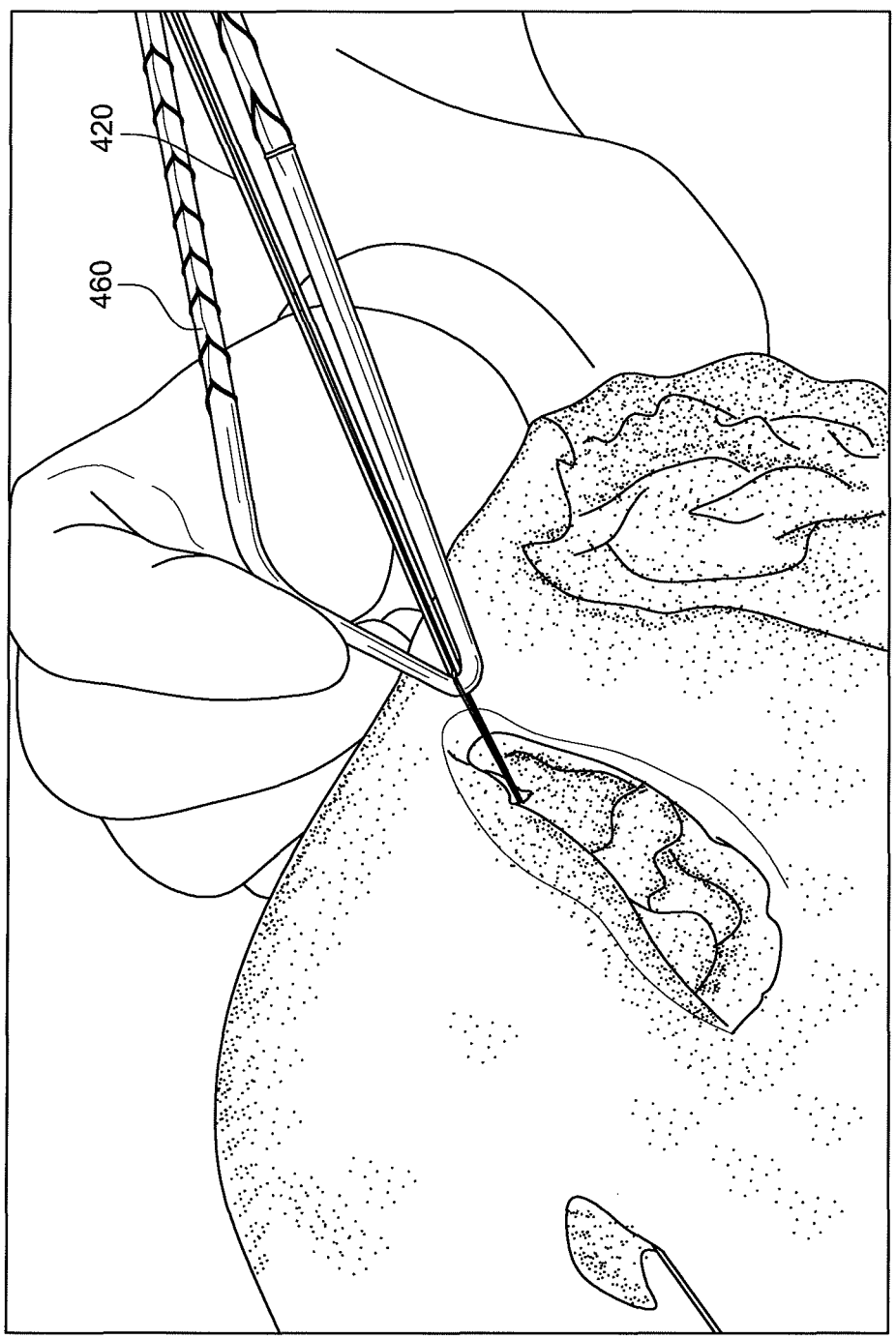

As shown in FIG. 22, a graft 460 and suture tape 420 are both looped through a pull suture.

Figure 23:
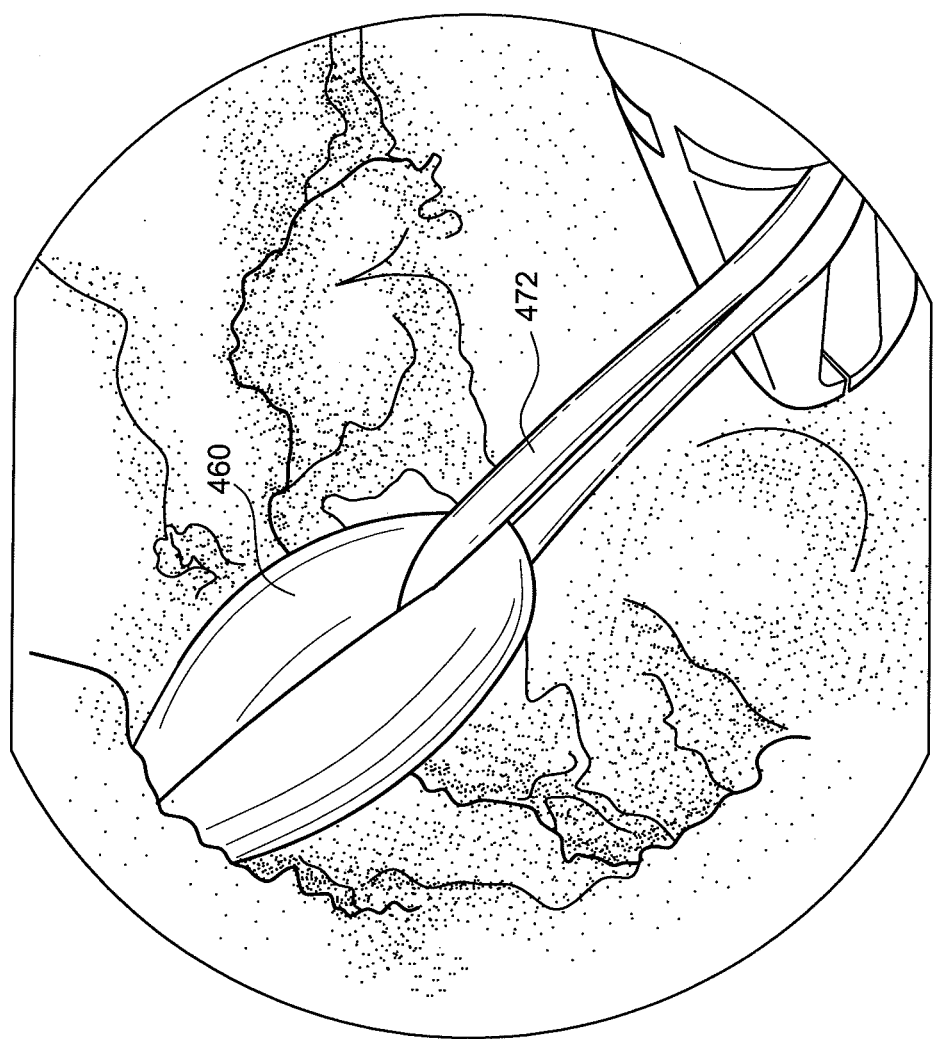

The suture 472 is used to pull the graft 460 and the suture tape 420 down through the coracoid tunnel as shown in FIG. 23 (all that can be seen is the graft material 460 as the suture tape 420 is enveloped by the graft material 460).

Figure 24:
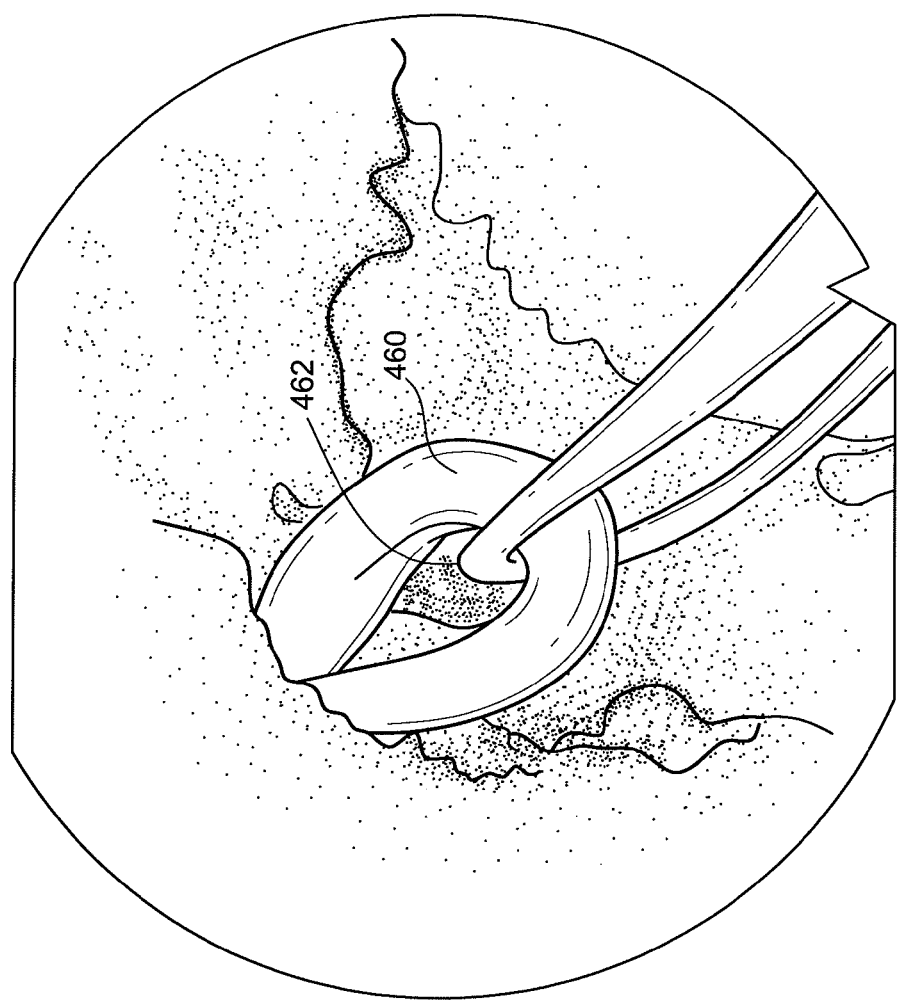

The dog bone shaped button 10 is engaged from subcoracoid space (rather than pulling the graft all the way up through the anterior portal). Referring to FIG. 24, a KingFisher™ instrument, sold by Arthrex, Inc., is used to open up a hole 462 (loop 462) in the graft 460 and the suture tape 420.

Figure 25:
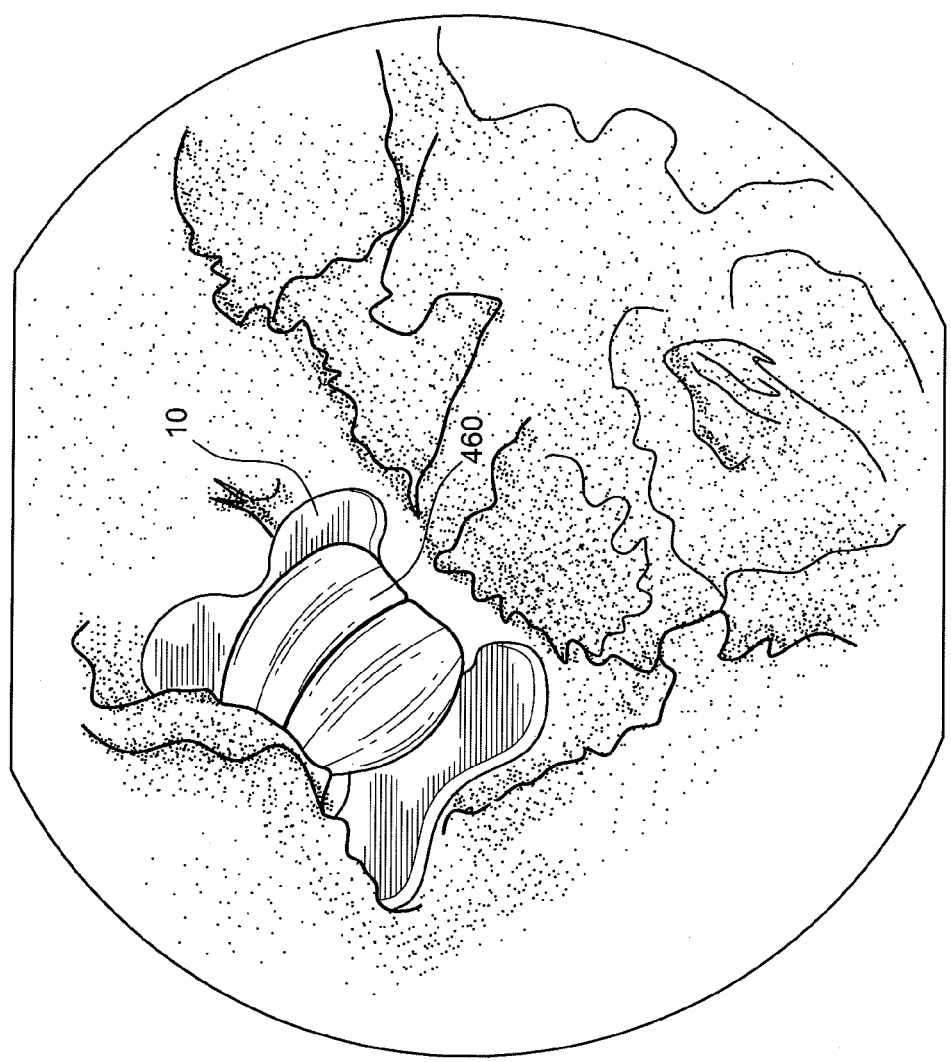

As shown in FIG. 25, a grasper is used to place the dog bone shaped button 10 through the suture tape loop 462 and the graft loop 462. The button 10 is turned and both limbs are pulled to secure the button 10 under the coracoid (matching the contour of the coracoid).

Figure 26:
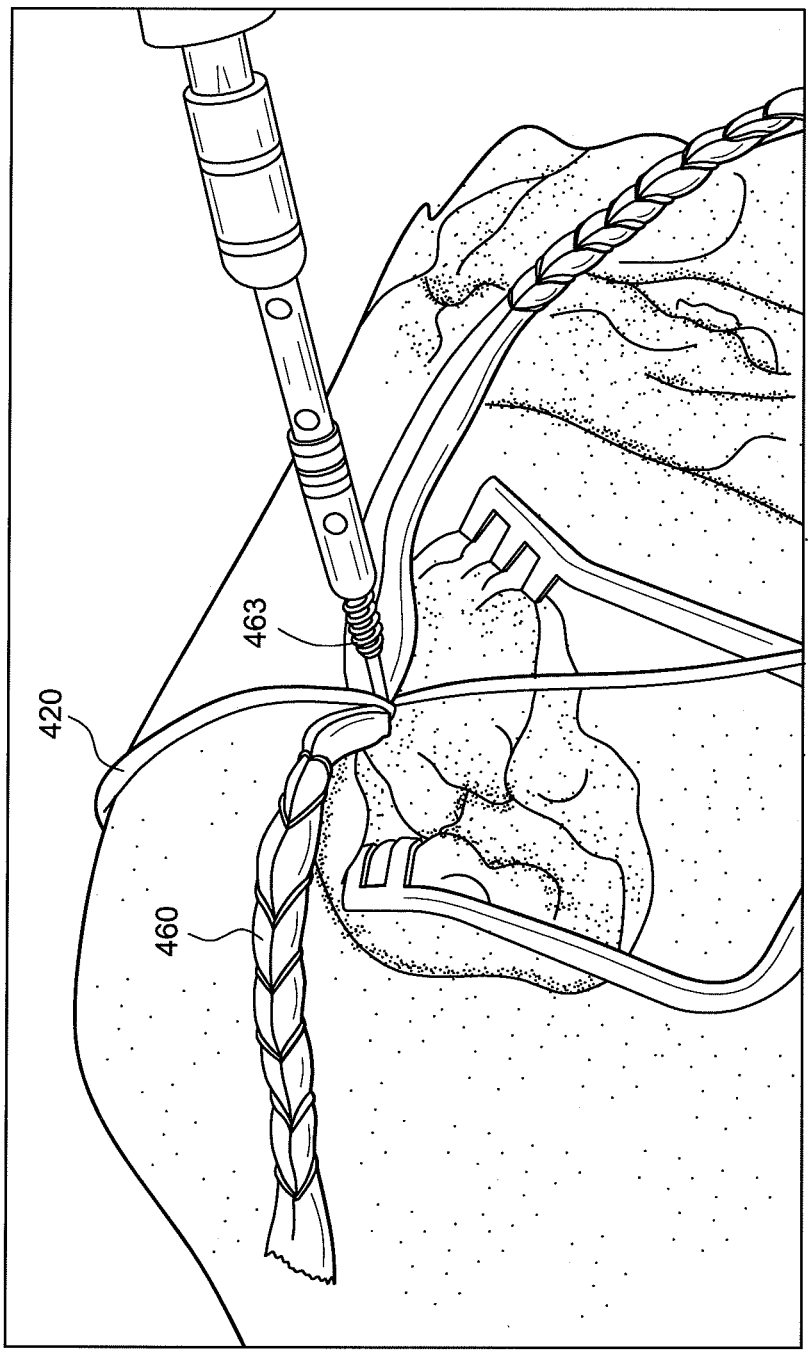

As shown in FIG. 26, the dog bone shaped button 10 is secured in the clavicle over a fixation device 463, for example an interference screw 463.

Figure 27:
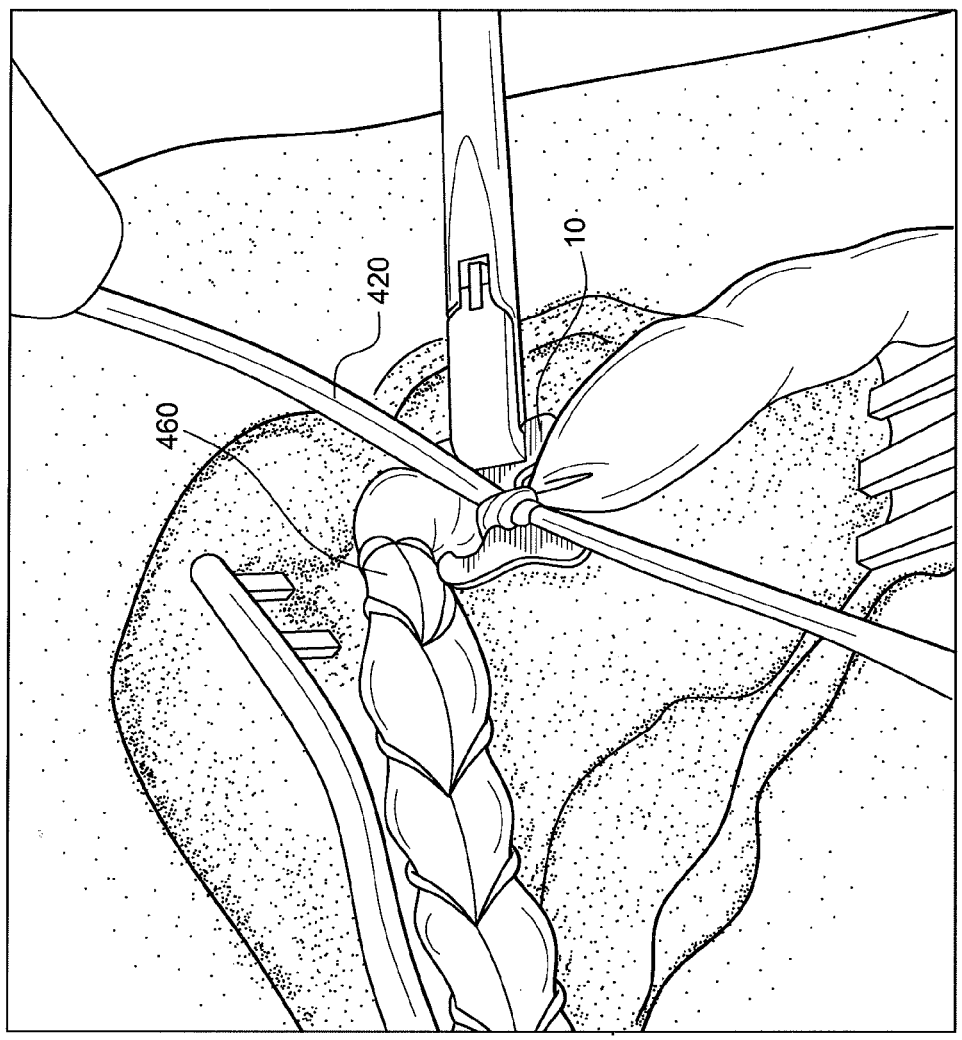

Referring to FIG. 27, secondary fixation of the dog bone shaped button 10 is obtained by first tying the suture tape 420 over the button 10 to achieve excellent compression.

Figure 28:
Figure 29:
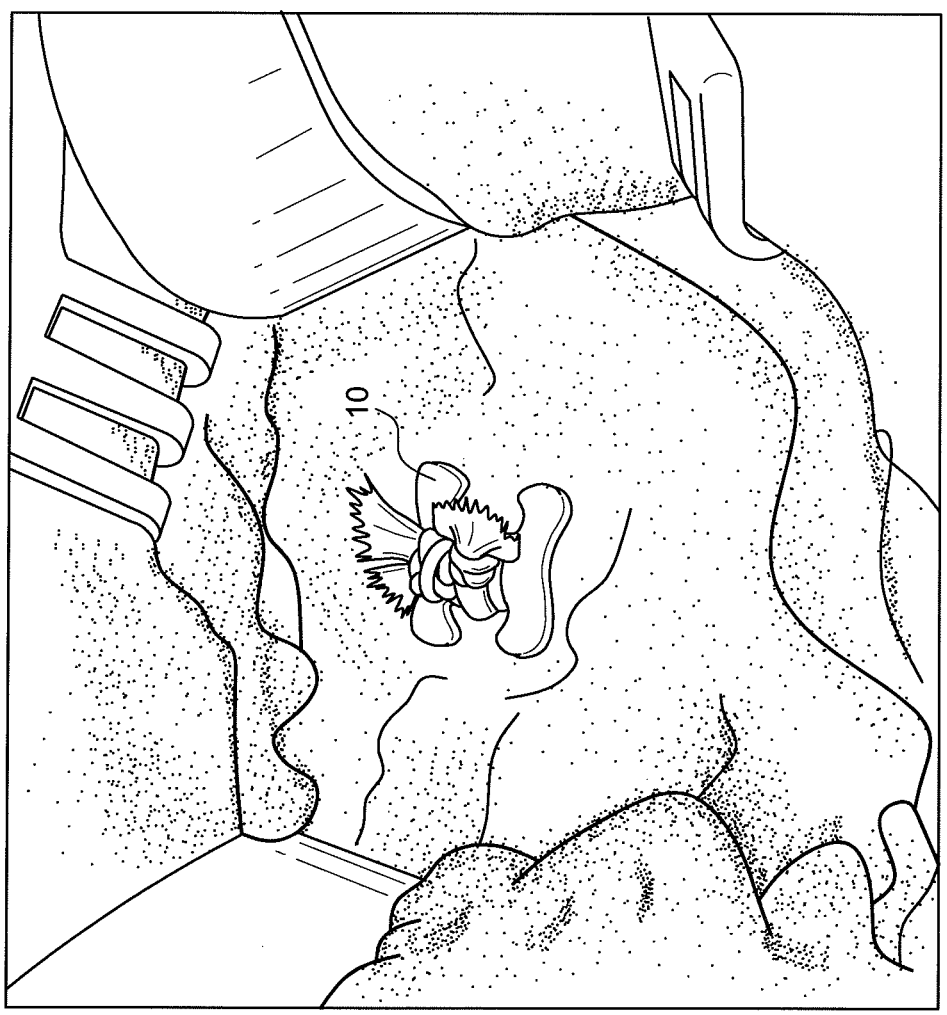

As shown in FIG. 28, the two limbs of the graft 460 are passed over one another, and then over the dog bone shaped button 10, and the two limbs are tied together with a suture strand. FIG. 29 shows the final construct.

The dog bone shaped button and constructs of the present invention may be provided in various dimensions based on the procedure and the size of the drilled tunnel. The dog bone shaped button may be provided with a "safety suture" (for example, a 2-0 high strength suture) attached through a small hole in the button, which may be pulled out of the button once the procedure is completed. As noted above, the dog bone shaped button may be employed with various flexible strands and/or graft materials, for example, with one or more suture tapes, or with one suture tape and an allograft.

The dog bone shaped button 10 of the present invention may be also employed for surgical repairs other than the AC joint repairs detailed above. For example, dog bone shaped buttons may be employed for any tendon/ligament reattachment to bone, such as distal biceps repairs (in a 2-incision technique, with one tunnel instead of two tunnels), or ankle syndesmosis repairs (creating smaller bone tunnels which reduce the stress and the risk of fibula fracture) or patellar/quadriceps tendon rupture repairs (creating fewer bone tunnels).

Figure 30:
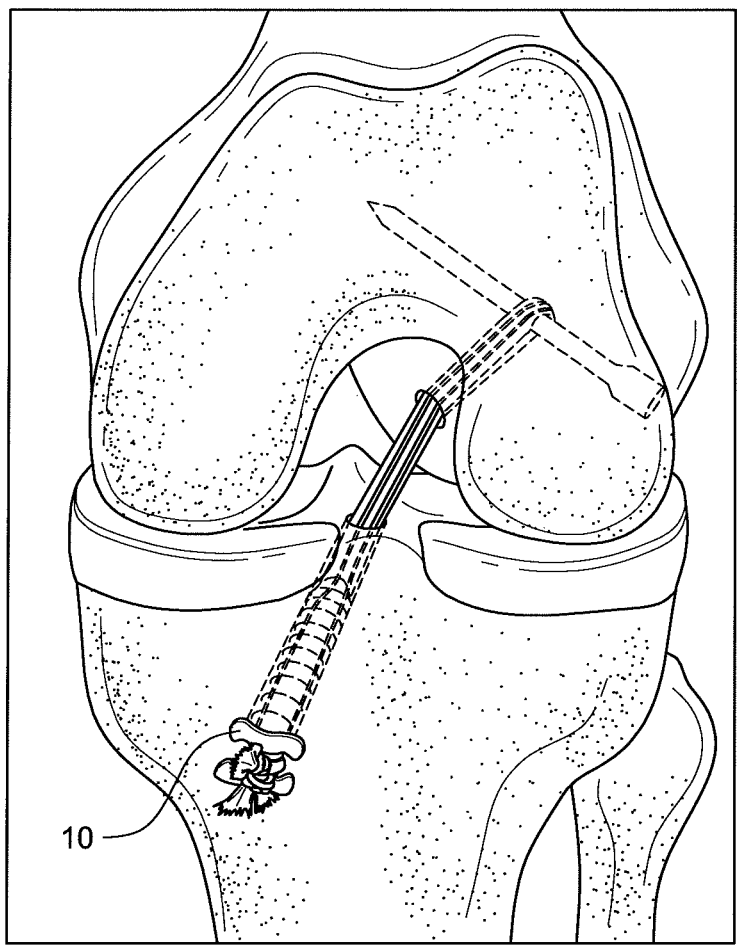
FIG. 30 illustrates a cross-pin ACL reconstruction repair with the "dog bone" shaped button of FIG. 1.

FIG. 30 illustrates an exemplary cross-pin ACL reconstruction repair with the dog bone shaped button 10 of the present invention. In this exemplary only technique, the suture tape is passed together with the graft (allograft), i.e., the suture tape is passed inside the allograft. The suture tape limbs are then passed over the dog bone shaped button 10, after tibial interference fixation, providing increased strength of the final construct.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed as new and desired to be protected by Letters Patent of the United States is:

1. A method for internal fixation of acromioclavicular joint dislocations, comprising in order the steps of:
providing an internal fixation system comprising a first fixation device with a first configuration having a first plurality of slotted openings, a second fixation device with a second configuration having a second plurality of slotted openings, and a suture loop construct between the first and second fixation devices, the suture loop construct being passed through the first plurality of slotted openings such that one end of a flexible loop engages the first fixation device and attaches to the first fixation device,
wherein the first fixation device is an elongated suture button having an elongated body with the first configuration, the first configuration being a dog bone shaped configuration comprising two lobes at each end of the elongated body, the elongated body including two slotted openings separated by a middle portion, the slotted openings extending from an outer circumference of the elongated body and to a plurality of apertures, the slotted openings allowing the suture loop construct to pass through the elongated body;
attaching the first fixation device to the suture loop construct by passing the flexible loop through the two slotted openings and through the plurality of apertures of the elongated body so that the flexible loop engages the first fixation device;
passing the flexible loop through clavicle and coracoid tunnels;
pulling the flexible loop to secure the first fixation device underneath the coracoid;
cutting an end of the flexible loop to create limbs;
securing the second fixation device over the clavicle tunnel by securing the limbs to the second fixation device; and
reducing the distance between the clavicle and the coracoid by traction of the suture loop construct.

2. The method of claim 1, further comprising:
drilling tunnels through the coracoid and clavicle; and
passing a tail end of the suture loop construct through the clavicle and coracoid tunnels after the flexible loop engages the first fixation device and before creating the limbs.

3. The method of claim 1, wherein the first fixation device has a concavity that approximates the convexity of the undersurface of the coracoid.

4. The method of claim 1, wherein the second configuration is a dog bone shaped configuration having a concavity that approximates the convexity of the upper surface of the clavicle.

5. A method for internal fixation of acromioclavicular joint dislocations, comprising in order the steps of:
drilling tunnels through the coracoid and clavicle;
passing a suture tape and a graft through the clavicle and coracoid tunnels;
opening up a hole in the suture tape and the graft and placing a first fixation device comprising a body with slotted openings through the hole in the suture tape and graft to secure the first fixation device under the coracoid, wherein the first fixation device is an elongated suture button with a dog bone shaped configuration comprising an elongated body and two lobes at each end of the elongated body, the slotted openings of the elongated body being separated by a middle portion, the slotted openings extending from an outer circumference of the elongated body and to a plurality of apertures, the slotted openings allowing the suture tape to pass through the plurality of apertures of the elongated body;
securing a second fixation device comprising an elongated body with slotted openings over the clavicle and an interference screw, wherein the second fixation devices is a suture button with a dog bone shaped configuration comprising an elongated body with slotted openings and two lobes at each end of the elongated body, the slotted openings of the elongated body being separated by a middle portion, the slotted openings extending from an outer circumference of the elongated body and to a plurality of apertures, the slotted openings allowing the suture tape to pass through the elongated body; and
providing secondary fixation of the first fixation device under the coracoid by tying suture tape limbs over the first fixation device to get compression, passing limbs of the graft over one another, and over the first fixation device, and tying the graft limbs together.

6. The method of claim 5, wherein the first fixation device has a concavity that approximates the convexity of the undersurface of the coracoid.

7. The method of claim 5, wherein the second fixation device has a concavity that approximates the convexity of the upper surface of the clavicle.

8. A method for internal fixation of acromioclavicular joint dislocations, comprising in order the steps of:
providing an internal fixation device comprising a first member with a first configuration and provided with a plurality of first apertures; a second member with a second configuration and provided with a plurality of second apertures; and a flexible fused suture construct between the first and second members, the flexible fused suture construct being looped through the plurality of first and second apertures, the flexible fused suture construct comprising at least two separate and independent suture strands or suture tapes connected together at a midpoint of each of the suture strands or suture tapes, resulting in multiple limbs of suture strands or tapes of equal length, wherein at least one of the first and second members is a button having a dog bone shape;

securing the first and second members on or adjacent to the clavicle and the coracoid, respectively; and reducing the distance between the clavicle and the coracoid by traction of the flexible fused suture construct.

9. The method of claim 8, further comprising the steps of:

forming a first hole through the clavicle and a second hole through the coracoid;

attaching the first member to the fused suture construct;

advancing the fused suture construct through the first and second holes, so that the first member engages a surface of the coracoid; and engaging the second member to the fused suture construct.

10. The method of claim 8, wherein the fused suture construct consists essentially of four limbs of suture tape having about equal length.

* * * * *